(12) United States Patent
Chan et al.

(10) Patent No.: US 7,228,583 B2
(45) Date of Patent: Jun. 12, 2007

(54) ELECTRIC TOOTHBRUSH HOUSING DESIGN

(75) Inventors: John Geoffrey Chan, Loveland, OH (US); John Roy Whitney, Hamilton, OH (US); Patrick William Brown, Auburn, OH (US)

(73) Assignee: Church & Dwight Co., Inc., Princeton, NJ (US)

( * ) Notice: Subject to any disclaimer, the term of this patent is extended or adjusted under 35 U.S.C. 154(b) by 170 days.

(21) Appl. No.: 10/659,101

(22) Filed: Sep. 10, 2003

(65) Prior Publication Data

US 2004/0128779 A1 Jul. 8, 2004

Related U.S. Application Data

(60) Provisional application No. 60/410,903, filed on Sep. 13, 2002.

(51) Int. Cl.
*A61C 17/22* (2006.01)
*A46B 5/02* (2006.01)

(52) U.S. Cl. .................................. 15/22.1; 15/143.1

(58) Field of Classification Search .............. 15/143.1, 15/167.1, 22.1; D4/138
See application file for complete search history.

(56) References Cited

U.S. PATENT DOCUMENTS

| | | | |
|---|---|---|---|
| D375,204 S | 11/1996 | Okada | |
| D382,407 S | 8/1997 | Craft et al. | |
| 5,735,012 A * | 4/1998 | Heinzelman et al. | 15/167.1 |
| D406,465 S * | 3/1999 | Barton et al. | D4/138 |
| 6,000,083 A | 12/1999 | Blaustein et al. | |
| D432,312 S | 10/2000 | Blaustein et al. | |
| D433,814 S | 11/2000 | Blaustein et al. | |
| 6,178,579 B1 | 1/2001 | Blaustein et al. | |
| 6,189,693 B1 | 2/2001 | Blaustein et al. | |
| 6,234,798 B1 * | 5/2001 | Beals et al. | 433/216 |
| 6,311,837 B1 | 11/2001 | Blaustein et al. | |
| D453,626 S | 2/2002 | Greene | |
| D454,251 S | 3/2002 | De Swarte et al. | |
| D454,695 S | 3/2002 | Greene | |
| 6,360,395 B2 | 3/2002 | Blaustein et al. | |
| 6,371,294 B1 | 4/2002 | Blaustein et al. | |
| 6,390,818 B2 | 5/2002 | Ferranti | |
| 6,401,290 B1 * | 6/2002 | Barton et al. | 15/143.1 |
| 6,422,867 B2 * | 7/2002 | Lang et al. | 433/118 |
| 6,601,272 B2 * | 8/2003 | Stvartak et al. | 16/430 |
| 2002/0032941 A1 | 3/2002 | Blaustein et al. | |
| 2003/0005533 A1 * | 1/2003 | Woodnorth et al. | 15/143.1 |
| 2003/0044313 A1 | 3/2003 | Lee | |
| 2003/0070259 A1 * | 4/2003 | Brown et al. | 16/436 |

(Continued)

FOREIGN PATENT DOCUMENTS

DE 201 09 552 U1 8/2001

(Continued)

*Primary Examiner*—Randall Chin
(74) *Attorney, Agent, or Firm*—K. Bradford Adolphson

(57) ABSTRACT

An improved housing for an electric toothbrush is disclosed. The improved housing provides two symmetrically positioned gripping members which assist the user in grasping the toothbrush particularly during brushing. Each of the gripping members includes a recessed gripping region having particular dimensional characteristics. The two gripping members are symmetrically arranged on the rearward sides of the toothbrush so that the brush may be used by both left-handed and right-handed individuals. A third gripping member may also be provided along the housing of the toothbrush.

10 Claims, 4 Drawing Sheets

U.S. PATENT DOCUMENTS

2003/0101526 A1 6/2003 Reick et al.
2005/0278874 A1* 12/2005 Blaustein et al. ............ 15/22.1

FOREIGN PATENT DOCUMENTS

| | | |
|---|---|---|
| FR | 2 796 831 A1 | 2/2001 |
| GB | 2 317 555 A1 | 4/1998 |
| WO | WO 99/44465 A1 | 10/1999 |
| WO | WO 01/17391 A1 | 3/2001 |
| WO | WO 01/29128 A1 | 4/2001 |

* cited by examiner

ELECTRIC TOOTHBRUSH HOUSING DESIGN

CROSS REFERENCE TO RELATED APPLICATION

This application claims the benefit of U.S. Provisional Application No. 60/410,903, filed Sep. 13, 2002, the substance of which is incorporated herein by reference.

FIELD OF THE INVENTION

The present invention relates to electric toothbrushes and more particularly, improved housing designs for electric toothbrushes.

BACKGROUND OF THE INVENTION

Prior artisans have proposed a wide variety of designs for electric toothbrush housings and handles. Many of these designs provide a collection of ridges extending in a direction either parallel to the longitudinal axis of the housing, such as in U.S. Des. Pat. Nos. 375,204 and 454,251; or generally perpendicular to that axis as in 382,407. In addition to certain aesthetic qualities that a collection of parallel ridges may provide, providing such ridges may also serve to promote gripping of the housing by a user, particularly during use of the toothbrush. Although satisfactory in many respects, collections of ridges along the exterior of a toothbrush may promote build-up of dentifrice and other agents over a period of time within crevices along the ridges. Accordingly, housing designs that emphasize a generally smooth outer surface, are favored.

It has been recognized in the art that improved handle designs for electric toothbrushes are needed. Proper handling and orientation of an electric toothbrush during use requires a handle contour that is well matched to a user's hand, and a surface having a relatively low tendency for slippage when being grasped. U.S. Pat. No. 6,390,818 addressed the need for an ergonomic grip for a dental instrument. However, that device is for a sleeve that may be fitted over a dental tool, such as may be used by a dental professional. And so, that device is not readily applicable to the field of electric toothbrushes, and particularly those that are directed for widespread retail sale to consumers.

Although the design of the '818 patent is satisfactory in many respects, other artisans have proposed different housing designs. Many of these designs utilize a flat region along a portion of the housing length. A flat region may facilitate gripping of the housing since such region disrupts the otherwise smooth contour of the otherwise cylindrical housing. However, depending upon the orientation of the brush head, such a flat region may actually hinder gripping of the housing. Furthermore, the orientation of the flat region with respect to the brush head may or may not be desirable depending upon which hand the user is holding the brush with. Examples of such housings with one or more flat regions include U.S. Des. Pat. Nos. 453,626 and 454,695. Accordingly, a need remains for an improved housing for an electric toothbrush.

SUMMARY OF THE INVENTION

The present invention achieves all the foregoing objectives and provides, in a first aspect, an electric toothbrush comprising a housing formed from a first material and including a handle, a brush head, and a neck extending between the handle and the brush head. The housing further includes a first gripping member disposed along an exterior region of the housing. The first gripping member is formed from a second material softer than the first material. The first gripping member defines a first recessed region. The toothbrush also comprises a second gripping member disposed along an exterior region of the housing. The second gripping member is also formed from the second material. The second gripping member defines a second recessed region.

In another aspect, the present invention provides an electric toothbrush comprising a housing having a handle, a brush head, and a neck extending between and integrally formed with the handle and the brush head. The housing defines a hollow interior region. The electric toothbrush further comprises two gripping members symmetrically disposed on the housing with respect to a longitudinal axis of the housing. Each of the gripping members is formed from a material selected from the group consisting of elastomers and rubber-based materials, and having a Shore A hardness of from about 30 to about 99.

In a further aspect, the present invention provides an electric toothbrush comprising a housing including a handle, a brush head, and a neck extending between and integrally formed with the handle and the brush head. The toothbrush also comprises a first and a second gripping member symmetrically disposed on the housing and with respect to a longitudinal axis of the housing. The first gripping member has a length of from about 25 mm to about 65 mm, and a width of from about 12 mm to about 25 mm. Each of the gripping members defines a corresponding recessed region.

BRIEF DESCRIPTION OF THE DRAWINGS

The present invention may take form in various components and arrangements of components, and in various techniques, methods, or procedures and arrangements of steps. The referenced drawings are only for purposes of illustrating preferred embodiments, they are not necessarily to scale, and are not to be construed as limiting the present invention.

It is believed that the present invention will be better understood from the following description taken in conjunction with the accompanying drawings in which.

DETAILED DESCRIPTION OF THE PREFERRED EMBODIMENTS

Figure 1:
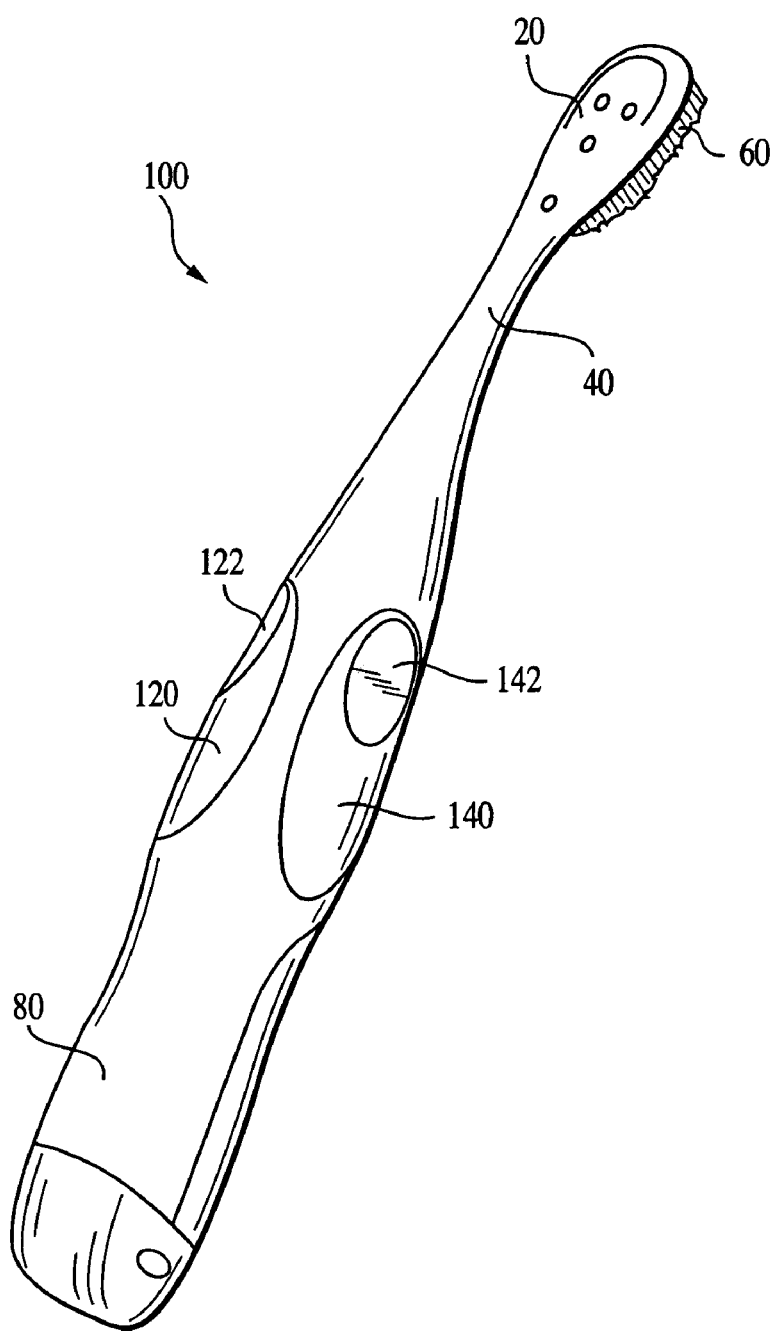
FIG. 1 is a perspective view of a preferred embodiment toothbrush illustrating two preferred gripping members in accordance with the present invention.
Figure 2:
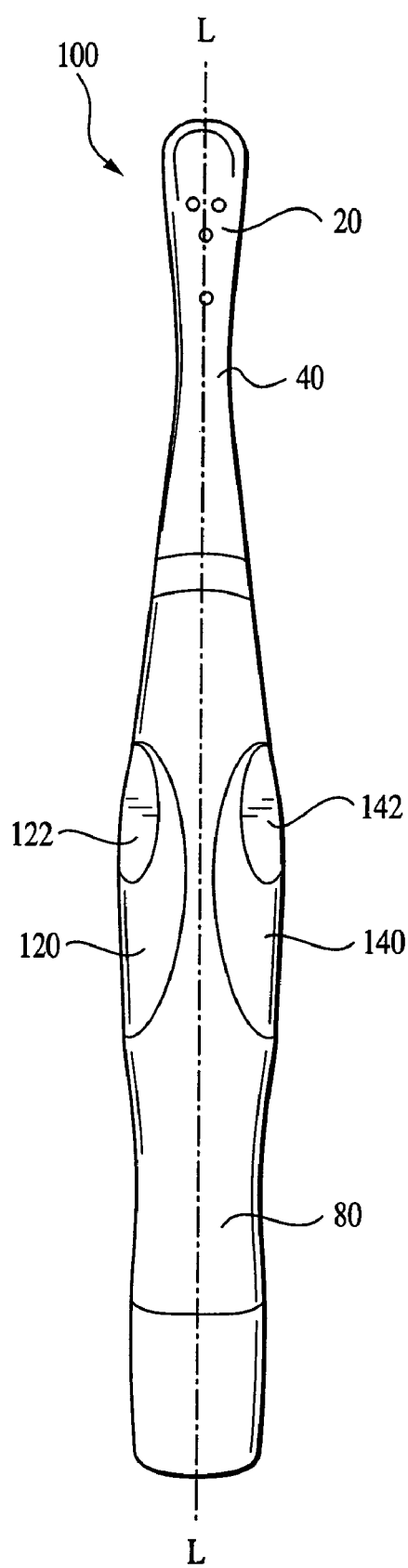
FIG. 2 is a rear view of the preferred embodiment toothbrush in accordance with the present invention.
Figure 3:
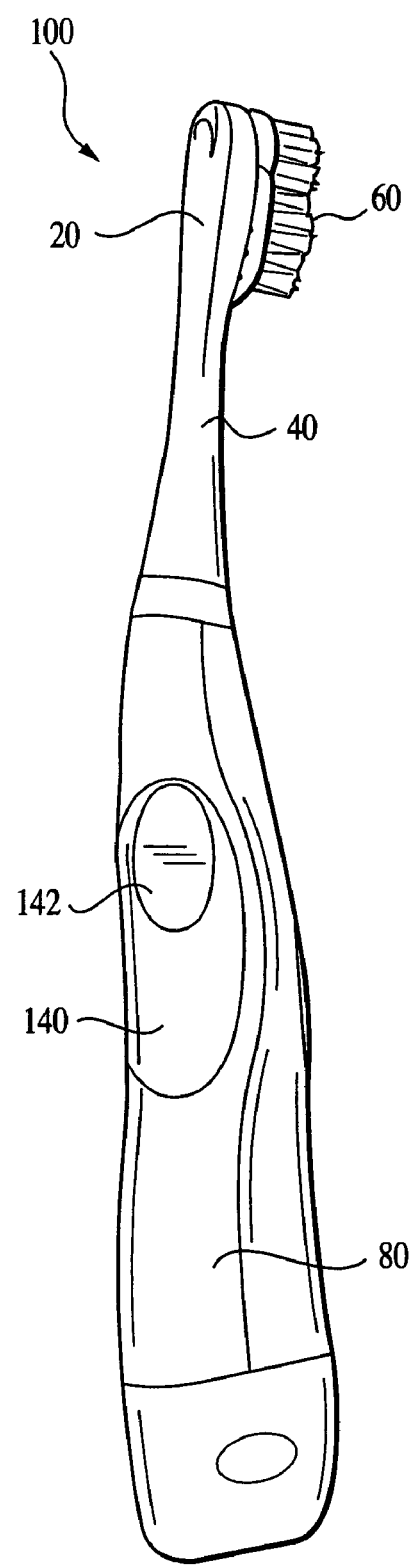
FIG. 3 is a side view of the preferred embodiment toothbrush in accordance with the present invention.

FIGS. 1–3 illustrate a preferred embodiment toothbrush 100 in accordance with the present invention. The preferred embodiment toothbrush 100 comprises a handle 80, a brush head 20, and a neck 40 extending therebetween and preferably integrally joined with both the handle 80 and the head 20. Disposed on the head 20 are a plurality of bristles 60. These bristles may include stationary bristles or movable bristles. By movable bristles, it is meant bristles that are powered or otherwise operatively engaged with a motor and drive mechanism generally housed within the body or handle 80 of the toothbrush. Disposed along the rear and lateral sides of the body of the toothbrush 100, preferably in the region of the handle 80 and/or the handle 80 and the neck 40, are two gripping members 120 and 140. These gripping members are formed of a softer material than the relatively rigid material forming the handle 80, neck 40, and brush head 20 of the toothbrush 100. A first gripping member 120 is disposed on one rearward side region of the brush 100, and a second gripping member 140 is disposed on a second rearward side of the toothbrush 100. This is shown in FIG. 2. It can be seen that the two gripping members 120 and 140 are preferably symmetrically positioned with respect to each other and with respect to a longitudinal axis L (shown in FIGS. 2 and 7) of the toothbrush 100. Each of the gripping members 120 and 140 extends along a portion of the rear face of the brush as shown in FIG. 2 and as illustrated in FIG. 3, preferably extends around a portion of the handle 80 to a side of the toothbrush 100.

Each of the gripping members 120 and 140 defines a recessed gripping region 122 and 142, respectively. These recessed regions are preferably formed or defined within each of the gripping members 120 and 140.

Figure 4:
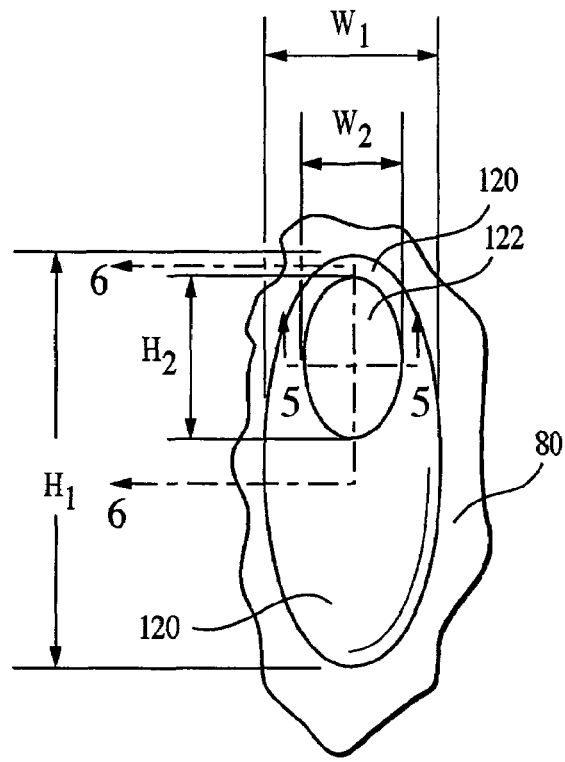
FIG. 4 is a detailed view of a preferred embodiment gripping member in accordance with the present invention.

FIG. 4 illustrates in greater detail the gripping member 120. It will be appreciated that preferably, each of the gripping members is identical to the other, and so the following description given with regard to gripping member 120 applies to gripping member 140. Gripping member 120 is preferably in the form of an oval when viewed in planar fashion. That is, the oval has a major axis which preferably extends in a direction parallel with the longitudinal axis L of the brush 100. The length of the gripping member 120 along this major axis is designated as $H_1$ in FIG. 4. $H_1$ preferably is from about 25 mm to about 65 mm, and more preferably from about 40 mm to about 46 mm. All measurements or dimensions given herein are taken along the surface of the object being measured unless indicated otherwise. The overall or maximum width of the gripping member 120, shown in FIG. 4 as $W_1$, is from about 12 mm to about 25 mm, and preferably from about 15 mm to about 22 mm. As noted, the gripping member 120 defines a recessed gripping region 122. Preferably, the region 122 is also in the shape of an oval when viewed in planar fashion as shown in FIG. 4. The gripping region 122 preferably has a length designated in FIG. 4 as $H_2$. $H_2$ ranges from about 25 mm to about 38 mm, and more preferably from about 18 mm to about 25 mm. The overall width of the gripping region 122, shown in FIG. 4 as $W_2$, is from about 9 mm to about 15 mm, and more preferably from about 10 mm to about 14 mm. It will be appreciated that the gripping region 122 is also in the form of an oval. However, the gripping region need not be concentrically defined within the gripping member 122. As can be seen in FIG. 4, the gripping region 122 is offset from the center of the gripping member 120. When each of the gripping members 120 and 140 are installed and secured, or otherwise formed, along the housing 80 of the toothbrush 100, as shown in FIG. 1, for instance, the gripping region 122 is preferably disposed toward the brush head 20 rather than the opposite end of the brush 100.

Figure 5:
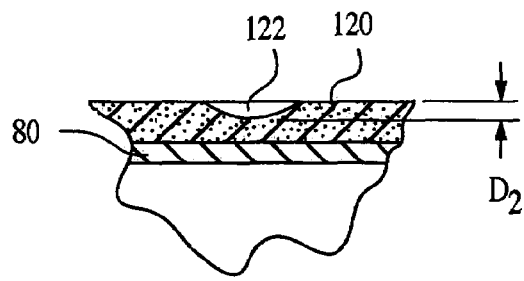
FIG. 5 is a partial cross-sectional view of the gripping member taken along line 5—5 shown in FIG. 4.
Figure 6:
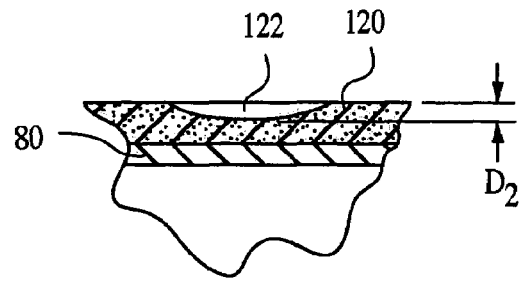
FIG. 6 is another partial cross-sectional view of the gripping member taken along line 6—6 shown in FIG. 4.

FIGS. 5 and 6 are partial cross-sectional details of the gripping member 120 shown in FIG. 4. Specifically, FIG. 5 is a partial cross-sectional view taken along line 5,5 of the gripping member 120 shown in FIG. 4. And, FIG. 6 is a partial cross-sectional view taken along line 6,6 shown in FIG. 4. Each of FIGS. 5 and 6 show the depressed or recessed gripping region 122 defined in the gripping member 120. The amount or degree of depression extends to a maximum depth of $D_2$ as shown in FIGS. 5 and 6. $D_2$ ranges from about 3 mm to about 10 mm and preferably from about 5 mm to about 8 mm.

The present invention is based, in part, upon the identification of particular dimensions and combinations of dimensions for the first and second gripping members and the recessed regions defined therein. The noted dimensions have been found to offer particularly beneficial and favorable ergonomic aspects. Moreover, the symmetrical feature when utilizing two oppositely positioned gripping members provides enhanced usability and functionality for the toothbrush.

Each of the gripping members 120 and 140 is preferably positioned at a location that is approximately in the middle or at a midpoint of the overall length of the toothbrush 100. Although a wide array of symmetrical placement configurations are encompassed by the present invention, it is preferred that each of the gripping members 120 and 140 is positioned at a location on the body or housing of the toothbrush 100 such that the midpoint of the overall length of the distal end of the brush head 20 to the distal-most region of the opposite handle end, falls within the recessed region of the gripping member.

Figure 7:
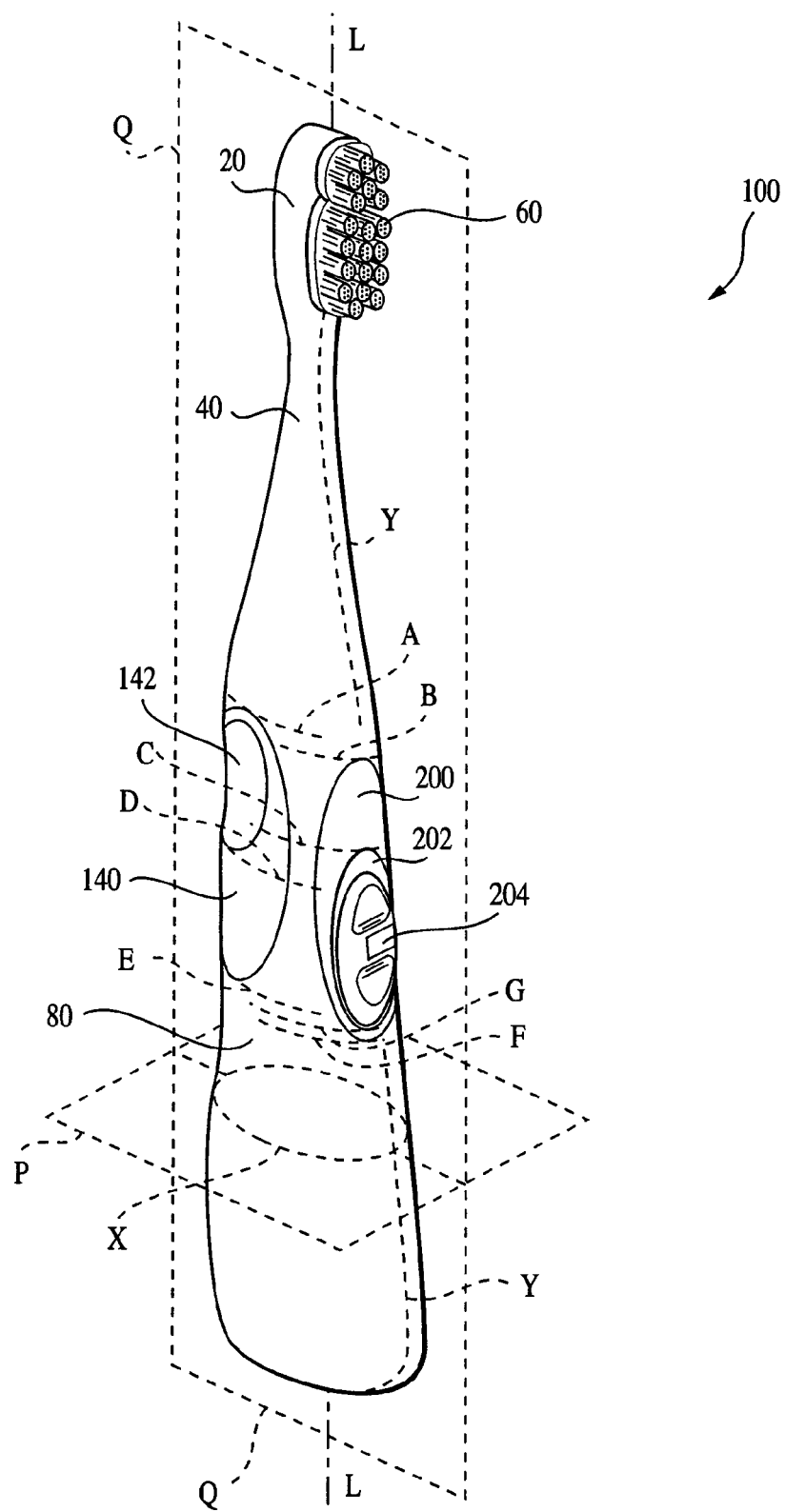
FIG. 7 is a perspective view of the preferred embodiment toothbrush illustrating a third gripping member along the front of the toothbrush.

FIG. 7 is a perspective view illustrating a front region of the preferred embodiment toothbrush 100. The toothbrush 100 also preferably includes a third gripping member 200 defining a recessed region 202. A movable switch or actuator 204 is preferably disposed and positionable within the recessed region 202. The movable actuator 204 governs operation of the toothbrush 100. Preferably, the third gripping member 200 surrounds the movable actuator 204 and most preferably, surrounds the actuator 204 regardless of its position within the recessed region 202.

The preferred toothbrush 100 utilizes a particular orientation and arrangement of the third gripping member 200 with respect to the first and second gripping members 120 and 140, respectively. This configuration can be understood by reference to FIG. 7 and noting various planes and lines shown thereon that intersect the toothbrush 100.

FIG. 7 illustrates a plane Q that extends along the longitudinal axis L of the toothbrush 100. Plane Q bisects the toothbrush 100 into essentially two halves, a first half and a second half. The plane Q intersects the toothbrush 100 across its entire length. The plane Q intersects the toothbrush 100 along a line Y shown in FIG. 7. Plane P also intersects the toothbrush 100, however, is oriented perpendicular to plane Q. The region of intersection of plane P and the toothbrush 100 is defined by line X shown in FIG. 7. This region of intersection corresponds to the cross-section of the toothbrush body at the point of intersection of plane P. In accordance with a feature of the present invention, it is preferred that the body of the toothbrush 100 generally exhibit an oval or oval-like cross-section across at least a majority of its length. Although the shape of the cross-section may change depending upon the location along the length of the toothbrush body at which plane P intersects such, it is generally preferred that this shape be oval in nature. Additionally, it is also preferred that the major axis of the oval extend within the plane Q, and so, also intersect the longitudinal axis L of the toothbrush 100.

FIG. 7 also illustrates various elevations or lines that extend about the outer periphery of the housing or body of the toothbrush 100 at various positions along its length. These lines are shown in FIG. 7 to better illustrate the relative position and orientation of the third gripping member 200 to each of the first and second gripping members 120 and 140, respectively. As previously noted, the relative positions of the first and second gripping members 120 and 140, respectively, are symmetrical and generally the same with respect to each other and their location along the body of the toothbrush 100. Accordingly, the following description of the position and orientation of the third gripping member 200 is given with respect to only the second gripping member 140 shown in FIG. 7.

The third gripping member 200 is preferably positioned along the frontward region or front face of the toothbrush 100. Preferably, the third gripping member 200 is symmetrically located along the front such that the line Y bisects the third gripping member 200 into two equal and corresponding halves. The third gripping member 200 is positioned slightly toward the end of the toothbrush 100 opposite the brush head 20 as compared to the location of the gripping member 140 along the length of the toothbrush body. That is, the end of the gripping member 200 closest to the brush head 20 is defined by line B. This line B is closer to the distal end of the brush opposite the brush head 20 than line A, which designates the distal-most end of the second gripping member 140 closest to the brush head 20. Similarly, the other end of the third gripping member 200, defined by line F, is closer to the end of the toothbrush 100 opposite the brush head 20, than the corresponding end of the second gripping member 140 defined by line E.

The recessed region 202 defined within the third gripping member 200 also has a preferred location along the exterior of the toothbrush 100 as follows. The distal end of the recessed region 202 closest to the brush head 20 is defined by line C and is closer to the brush head 20 than the end of the second recessed region 142 opposite the brush head 20, defined by line D. Furthermore, the opposite end of the recessed region 202 defined by line G is closer to the end of the toothbrush 100 opposite the brush head 20 than the distal end of the first gripping member 140 defined by line E. The result of this particular orientation of the recessed region 202 within the third gripping member 200 is such that the movable actuator 204 is off-center with respect to the length of the third gripping member, and preferably disposed closer toward the end of the toothbrush 100 opposite the brush head 20, than the center or midpoint of both the first and second gripping members 120 and 140.

The overall length as measured along line Y of the third gripping member 200 is preferably greater than the length of either the first or second gripping member 120 and 140, designated herein as $H_1$. Similarly, the overall length of the recessed region 202 defined along line Y is greater than the length of either of the recessed regions 122 or 142.

The preferred embodiment toothbrush 100 may also utilize additional gripping members at various regions along its housing or body. Furthermore, the present invention gripping members, i.e. the first, second, and third gripping members, are not limited to having oval shapes, nor are these members limited to the particular locations and orientations depicted in the accompanying figures. The present invention gripping members may be provided at various locations along the outer surface of the toothbrush body or housing. Furthermore, one or more of these gripping members may be oriented differently than shown in the referenced figures.

The materials for forming each of the gripping members 120, 140, and 200, are preferably materials that exhibit some degree of flexibility and pliability, and furthermore, which promote gripping along their outer surfaces. Examples of these materials include elastomers and rubber-based materials.

As noted, the material used for forming the first, second, and third gripping members 120, 140, and 200 is softer and more flexible than the material forming the housing of the toothbrush 100. Generally, the hardness of the material forming the housing exhibits a Shore D hardness of from about 30 to about 80, and more preferably from about 50 to about 70. Preferably, the material forming the gripping members 120, 140, and 200 exhibits a hardness of from about 30 to about 99, and more preferably from about 40 to about 70 as measured on the Shore A scale. It will be appreciated that the present invention is not limited to these particular hardnesses, and may utilize materials that are softer or harder.

A wide array of polymers may be used to form the housing 80 of the preferred embodiment toothbrush 100. In the following description of the preferred polymer materials for use herein, the abbreviations that are commonly used by those of skill in the art to refer to certain polymers appear in parentheses following the full names of the polymers. The polymer is preferably polypropylene ("PP"), or may be selected from the group consisting of other commercially available materials, such as polystyrene ("PS"), polyethylene ("PE"), acrylonitrile-styrene copolymer ("SAN"), and cellulose acetate propionate ("CAP"). These materials may be blended with one or more additional polymers including a thermoplastic elastomer ("TPE"), a thermoplastic olefin ("TPO"), a soft thermoplastic polyolefin (e.g., polybutylene), or may be selected from other elastomeric materials, such as ethylene-vinylacetate copolymer ("EVA"), and ethylene propylene rubber ("EPR"). Examples of suitable thermoplastic elastomers herein include styrene-ethylene-butadiene-styrene ("SEBS"), styrene-butadiene-styrene ("SBS"), and styrene-isoprene-styrene ("SIS"). Examples of suitable thermoplastic olefins herein include polybutylene ("PB"), and polyethylene ("PE").

In addition, color can be provided to give the toothbrush an aesthetically pleasing appearance. Opaque or translucent colors can be provided. For translucent brushes an insert can further be provided in the handle. Such inserts can be any color and are typically made from a polypropylene material.

Techniques known to those of skill in the art, such as injection molding, can be used to manufacture the toothbrush of the present invention.

The present invention may utilize features, aspects, components, materials, and characteristics from one or more of the following published patent applications or issued patents: WO 01/29128; U.S. Pat. No. 6,000,083; U.S. Des. Pat. No. 432,312; U.S. Des. Pat. No. 433,814; U.S. Pat. No. 6,178,579; U.S. Pat. No. 6,189,693; U.S. Pat. No. 6,311,837; U.S. published patent application Ser. No. 2002/0032941; U.S. Pat. No. 6,360,395; and U.S. Pat. No. 6,371,294; all of which are hereby incorporated by reference.

The foregoing description is, at present, considered to be the preferred embodiments of the present invention. However, it is contemplated that various changes and modifications apparent to those skilled in the art, may be made without departing from the present invention. Therefore, the foregoing description is intended to cover all such changes and modifications encompassed within the spirit and scope of the present invention, including all equivalent aspects.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An electric toothbrush comprising a housing formed from a first material and including a handle, a brush head, and a neck extending between said handle and said brush head and a positionable actuator disposed in said housing for controlling operation of said toothbrush, characterized in that said housing further includes a first gripping member disposed along an exterior region of said housing, said first gripping member formed from a second material softer than said first material, said first gripping member having a convex shape contoured to match said housing and a first substantially concave recessed region on an exposed exterior surface thereof, and a second gripping member having a convex shape contoured to match said housing and formed from said second material, said second gripping member defining a second substantially concave recessed region on an exposed exterior surface thereof, whereby said first and second recessed regions are useful in assisting a user to grasp the handle during use of the toothbrush, said first and second gripping members and said first and second substantially concave recessed regions thereof having oval shapes when viewed in a plan view, said first and second substantially concave, oval recessed regions are concavely shaped along both their major and minor axes.

2. The electric toothbrush of claim 1 wherein said housing of said toothbrush defines a longitudinal axis, and said first and said second gripping members are symmetrically disposed on said housing with respect to said longitudinal axis.

3. The electric toothbrush of claim 1 wherein said first gripping member has a length of from about 25 mm to about 65 mm, and a width of from about 12 mm to about 25 mm.

4. The electric toothbrush of claim 3 wherein said first recessed region has a length of from about 25 mm to about 38 mm, a width of from about 9 mm to about 15 mm, and a depth of from about 3 mm to about 10 mm.

5. The electric toothbrush of claim 1 wherein said second material has a Shore A hardness between about 30 and about 99.

6. The electric toothbrush of claim 1 wherein each of said first and second gripping members is formed from a material selected from the group consisting of elastomers and rubber-based materials.

7. The electric toothbrush of claim 1 wherein said first and second gripping members are separate and distinct from each other.

8. The electric toothbrush of claim 1 wherein said first and second gripping members are symmetrically disposed on a rearward side of said housing so that said toothbrush may be used by both left-handed and right-handed individuals.

9. An electric toothbrush comprising a housing formed from a first material and including a handle, a brush head, and a neck extending between said handle and said brush head and a positionable actuator disposed in said housing for controlling operation of said toothbrush, characterized in that said housing further includes a first gripping member disposed along an exterior region of said housing, said first gripping member formed from a second material softer than said first material, said first gripping member having a generally convex shape contoured to match said housing and a first substantially concave recessed region on an exposed exterior surface thereof, a second gripping member having a generally convex shape contoured to match said housing and formed from said second material, said second gripping member defining a second substantially concave recessed region on an exposed exterior surface thereof, whereby said first and second recessed regions are useful in assisting a user to grasp the handle during use of the toothbrush, said first and second gripping members and said first and second substantially concave recessed regions thereof having generally oval shapes when viewed in a plan view, and a third gripping member disposed along an exterior region of said housing between said first and second gripping members, said positionable actuator is disposed in said third gripping member.

10. The electric toothbrush of claim 9 wherein said third gripping member is formed from a material having a Shore A hardness between about 30 and about 99.

* * * * *